United States Patent
Butera et al.

(10) Patent No.: US 9,872,985 B2
(45) Date of Patent: Jan. 23, 2018

(54) GLUCOSE REGULATION VIA ELECTRICAL STIMULATION OF NERVES INNERVATING THE LIVER

(71) Applicant: GEORGIA TECH RESEARCH CORPORATION, Atlanta, GA (US)

(72) Inventors: Robert Butera, Decatur, GA (US); Yogi Anil Patel, Atlanta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 0 days.

(21) Appl. No.: 15/060,132

(22) Filed: Mar. 3, 2016

(65) Prior Publication Data
US 2016/0256683 A1 Sep. 8, 2016

Related U.S. Application Data

(60) Provisional application No. 62/127,328, filed on Mar. 3, 2015.

(51) Int. Cl.
*A61N 1/36* (2006.01)
*A61N 1/05* (2006.01)

(52) U.S. Cl.
CPC ....... *A61N 1/3606* (2013.01); *A61N 1/36053* (2013.01); *A61N 1/36139* (2013.01); *A61N 1/36171* (2013.01); *A61N 1/0551* (2013.01); *A61N 1/36085* (2013.01); *A61N 1/36157* (2013.01)

(58) Field of Classification Search
CPC .............. A61N 1/3606; A61N 1/36053; A61N 1/36139; A61N 1/0551
See application file for complete search history.

(56) References Cited

U.S. PATENT DOCUMENTS

| | | |
|---|---|---|
| 5,231,988 A | 8/1993 | Wernicke et al. |
| 6,135,978 A | 10/2000 | Houben et al. |
| 8,060,208 B2 | 11/2011 | Kilgore et al. |
| 2003/0181958 A1 | 9/2003 | Dobak, III |
| 2006/0190053 A1 | 8/2006 | Dobak |
| 2007/0106337 A1 | 5/2007 | Errico et al. |
| 2009/0254143 A1* | 10/2009 | Tweden ............. A61N 1/36007 607/40 |

(Continued)

FOREIGN PATENT DOCUMENTS

| | | |
|---|---|---|
| WO | 2004054606 | 7/2004 |
| WO | 2009124233 | 10/2009 |

OTHER PUBLICATIONS

International Search Report and Written Opinion issued in Application No. PCT/US16/20686, dated May 19, 2016 (11 pages).

(Continued)

*Primary Examiner* — Alyssa M Alter
(74) *Attorney, Agent, or Firm* — Meunier Carlin & Curfman LLC

(57) ABSTRACT

An example method for causing a perturbation of blood glucose level in a subject is described herein. The method can include selectively inhibiting neural activity of at least one of a hepatic branch of the subject's vagus nerve or the subject's greater splanchnic nerve using electrical stimulation having a frequency greater than about 5 kHz. The selective inhibition of neural activity causes the subject's blood glucose level to increase or decrease as compared to a baseline level.

20 Claims, 6 Drawing Sheets

(56) References Cited

U.S. PATENT DOCUMENTS

2016/0001082 A1    1/2016  Butera et al.

OTHER PUBLICATIONS

ClinicalTrials.gov; Identifier: NCT01117311; Vagal Nerve Stimulation and Glucose Metabolism (2013).

Niijima A., Control of liver function and neuroendocrine regulation of blood glucose levels, Integrative Functions of the autonomic nervous system; an analysis of the interrelationships and interactions of the sympathetic and parasympathetic, 1979, pp. 68-83. (9 pages).

Berthoud, H.-R. et al., Characteristics of gastric and pancreatic responses to vagal stimulation with varied frequencies: evidence for different fiber calibers?, Journal of the Autonomic Nervous System, 1987, vol. 19, pp. 77-84. (8 pages).

Jungermann, K. et al., Regulation of liver metabolism by the hepatic nerves, Advances in Enzyme Regulation, 1987, pp. 63-88. (27 pages).

Bhadra, N. et al., High-Frequency Electrical Conduction Block of Mammalian Peripheral Motor Nerve, Muscle Nerve, 2005, vol. 32, pp. 782-790. (9 pages).

Bhadra, N. et al., High frequency electrical conduction block of the pudendal nerve, J. Neural Eng., 2006, vol. 3, pp. 180-187. (8 pages).

\* cited by examiner

GLUCOSE REGULATION VIA ELECTRICAL STIMULATION OF NERVES INNERVATING THE LIVER

CROSS-REFERENCE TO RELATED APPLICATIONS

This application claims the benefit of U.S. provisional patent application No. 62/127,328, filed on Mar. 3, 2015, and entitled "GLUCOSE REGULATION VIA ELECTRICAL STIMULATION OF NERVES INNERVATING THE LIVER," the disclosure of which is expressly incorporated herein by reference in its entirety.

BACKGROUND

The liver is implicated in a variety of functions that contribute to homeostasis of systemic blood glucose levels. The hepatic branch of the vagus nerve is a sub-population of axons from the vagus nerve that innervate the liver along with the greater splanchnic nerves. Chemical and anatomical manipulation of the hepatic vagus has shown a change in systemic blood glucose levels over a range of time periods after manipulation. Manipulation is typically in the form of a nerve transection (i.e., cutting the nerve) so the nerves are no longer connected to the liver or via electrical stimulation (e.g., periodic perturbations) of the nerve. Electrical stimulation of the hepatic branch of the vagus nerve using low frequencies (up to 30 Hz) have shown higher systemic blood glucose levels within minutes of turning on the stimulation and vagotomy (i.e., cutting of the cervical vagus) studies have shown a decrease in systemic blood glucose levels hours after cutting the nerve. However, cutting of these nerves is permanent and not typically viable for clinical applications.

SUMMARY

Described herein are devices and methods for regulating systemic blood glucose via stimulation of a subject's nerves innervating the liver. The stimulation results in increases or decreases in neural activity in the hepatic vagus nerve and/or the greater splanchnic nerve, which cause increases or decreases in systemic blood glucose levels in the subject. The increase and/or decrease in nerve activity can be achieved by applying electrical stimulation with characteristics (e.g., frequencies, amplitudes, etc.) that can either (i) excite the nerve or (ii) inhibit indigenous electrical activity (which effectively inhibits the nerve). According to the devices and methods described herein, systemic blood glucose levels of a subject can be manipulated directly by altering liver uptake and release of glucose through electrical stimulation, which excites or inhibits nerve activity of either the hepatic branch of the vagus nerve and/or the greater splanchnic nerve.

Nerve activity is increased or decreased in the target nerves by electrically stimulating the nerves. By turning the electrical stimulation on or off to either increase or decrease nerve activity, it is possible to cause either an increase or a decrease in systemic blood glucose levels in the subject. The characteristics (e.g., frequency, current amplitude, etc.) of the electrical stimulation can be selected to cause an increase or decrease in nerve activity. Thus, electrical stimulation can be used to excite or inhibit either the hepatic vagus nerve and/or the greater splanchnic nerve to maintain blood glucose levels at a desirable level via manipulation of liver function. Additionally, when combined with a means of glucose measurement, it is possible to control which nerve to electrically stimulate (e.g., the hepatic vagus nerve or the greater splanchnic nerve), as well as whether or not to excite or inhibit the particular nerve. Such control can be used to maintain blood glucose levels at a desired set point, which may be set by a clinician or a user.

An example method for causing a perturbation of blood glucose level in a subject is described herein. The method can include selectively inhibiting neural activity of at least one of a hepatic branch of the subject's vagus nerve or the subject's greater splanchnic nerve using electrical stimulation having a frequency greater than about 5 kHz. The selective inhibition of neural activity causes the subject's blood glucose level to increase or decrease as compared to a baseline level.

Optionally, the method can further include selectively exciting neural activity of at least one of the hepatic branch of the subject's vagus nerve or the subject's greater splanchnic nerve using electrical stimulation. The selective excitation and inhibition of neural activity causes the subject's blood glucose level to increase or decrease as compared to the baseline level.

In some implementations, neural activity of the hepatic branch of the subject's vagus nerve can be selectively excited using electrical stimulation. Alternatively or additionally, in some implementations, neural activity of the subject's greater splanchnic nerve can be selectively inhibited using electrical stimulation having a frequency greater than about 5 kHz.

Alternatively or additionally, neural activity of at least one of the hepatic branch of the subject's vagus nerve or the subject's greater splanchnic nerve can be selectively inhibited using electrical stimulation having a frequency from about 5 kHz to about 100 KHz. Additionally, the electrical stimulation can optionally deliver a current with an amplitude from about 50 µA to about 50 mA.

Alternatively or additionally, neural activity of at least one of the hepatic branch of the subject's vagus nerve or the subject's greater splanchnic nerve can be selectively excited using electrical stimulation having a frequency from about 1 Hz to about 200 Hz. Additionally, the electrical stimulation can optionally deliver a current with an amplitude from about 50 µA to about 50 mA.

Alternatively or additionally, the method can further include administering a substance (e.g., a bolus of glucose) to the subject, measuring the subject's blood glucose level at each of a plurality of time intervals, adjusting one or more stimulation parameters based on the subject's measured blood glucose level, and altering a glucose load associated with the substance through the selective excitation or inhibition of neural activity. Optionally, the substance can be administered to the subject orally or through injection.

Alternatively or additionally, the selective excitation or inhibition of neural activity further causes a change in level of a metabolite or enzyme.

Alternatively or additionally, the method can further include providing a first electrode at a portion of the hepatic branch of the subject's vagus nerve and a second electrode at a portion of the subject's greater splanchnic nerve. For example, the first electrode can optionally be provided between the subject's liver and the subject's vagal trunk. Alternatively or additionally, the second electrode can optionally be provided between the subject's suprarenal ganglia and celiac ganglia.

Alternatively or additionally, the method can further include monitoring the subject's blood glucose level. Optionally, the method can further include controlling the selective excitation or inhibition of neural activity based on the subject's blood glucose level.

Alternatively or additionally, the method can further include controlling the selective excitation or inhibition of neural activity based on user input.

Alternatively or additionally, the method can further include controlling the selective excitation or inhibition of neural activity based on a predetermined time schedule.

Another example method for causing a perturbation of blood glucose level in a subject is described herein. The method can include providing a first electrode at a portion of a hepatic branch of the subject's vagus nerve, providing a second electrode at a portion of the subject's greater splanchnic nerve, providing a stimulus generator operably coupled with the first electrode and the second electrode, and using the stimulus generator, providing a first stimulus signal to the first electrode and providing a second stimulus signal to the second electrode. The first stimulus signal can be configured to energize the first electrode and excite neural activity of the hepatic branch of the subject's vagus nerve. The second stimulus signal can be configured to energize the second electrode and inhibit neural activity of the subject's greater splanchnic nerve.

Additionally, the subject's blood glucose level increases as compared to a baseline level in response to providing the first stimulus or providing the second stimulus signal. Alternatively or additionally, the subject's blood glucose level decreases as compared to a baseline level in response to providing the first stimulus signal or providing the second stimulus signal.

Alternatively or additionally, the first stimulus signal can be a waveform applied at a frequency from about 1 Hz to about 200 Hz. Optionally, the first stimulus signal can deliver a current with an amplitude from about 50 µA to about 50 mA.

Alternatively or additionally, the second stimulus signal can be a waveform applied at a frequency from about 1 kHz to about 100 kHz. Optionally, the second stimulus signal can deliver a current with an amplitude from about 50 µA to about 50 mA.

Alternatively or additionally, the first electrode or the second electrode can a monopolar, bipolar, or tripolar electrode. Alternatively or additionally, the first electrode is located between the subject's liver and the subject's vagal trunk. Alternatively or additionally, the second electrode can be located between the subject's suprarenal ganglia and celiac ganglia.

Alternatively or additionally, the stimulus generator can be a voltage source or a current source.

Alternatively or additionally, at least one of the first electrode, the second electrode, or the stimulus generator can be implanted in the subject's body.

Alternatively or additionally, the method can further include providing a glucose sensor for monitoring the subject's blood glucose level. Optionally, the glucose sensor can be implanted in the subject's body.

Alternatively or additionally, the method can further include providing a control unit operably coupled with the stimulus generator. The control unit can optionally be configured to receive a user input and, in response to the user input, transmit a control signal to the stimulus generator to initiate providing the first stimulus signal or the second stimulus signal. Alternatively or additionally, the control unit can optionally be configured to transmit at predetermined time intervals a control signal to the stimulus generator to initiate providing the first stimulus signal or the second stimulus signal. Alternatively or additionally, the control unit can optionally be configured to transmit at a predetermined blood glucose level a control signal to the stimulus generator to initiate providing the first stimulus signal or the second stimulus signal. Optionally, the predetermined blood glucose level can be adjustable by a user.

Alternatively or additionally, the control unit further can optionally include at least one of a display device or an interface device.

An example device for causing a perturbation of blood glucose level in a subject is described herein. The device can include a first electrode configured to attach to a portion of a hepatic branch of the subject's vagus nerve, a second electrode configured to attach to a portion of the subject's greater splanchnic nerve, and a stimulus generator operably coupled with the first electrode and the second electrode. The stimulus generator can be configured to provide stimulus signals to at least one of the first electrode and the second electrode. The device can further include a control unit operably coupled with the stimulus generator. The control unit can be configured to control the stimulus generator to: provide a first stimulus signal configured to selectively excite neural activity of at least one of the hepatic branch of the subject's vagus nerve or the subject's greater splanchnic nerve, and provide a second stimulus signal having a frequency greater than about 5 kHz and configured to selectively inhibit neural activity of at least one of the hepatic branch of the subject's vagus nerve or the subject's greater splanchnic nerve. The selective excitation and inhibition of neural activity causes the subject's blood glucose level to increase or decrease as compared to a baseline level.

Another example device for causing a perturbation of blood glucose level in a subject is described herein. The device can include a first electrode configured to attach to a portion of a hepatic branch of the subject's vagus nerve, a second electrode configured to attach to a portion of the subject's greater splanchnic nerve, and a stimulus generator operably coupled with the first electrode and the second electrode. The stimulus generator can be configured to provide stimulus signals to at least one of the first electrode and the second electrode. The device can further include a control unit operably coupled with the stimulus generator. The control unit can be configured to control the stimulus generator to: provide a first stimulus signal to the first electrode and provide a second stimulus signal to the second electrode. The first stimulus signal can be configured to excite neural activity of the hepatic branch of the subject's vagus nerve, and the second stimulus signal can be configured to inhibit neural activity of the subject's greater splanchnic nerve.

It should be understood that the above-described subject matter may also be implemented as a computer-controlled apparatus, a computer process, a computing system, or an article of manufacture, such as a computer-readable storage medium.

Other systems, methods, features and/or advantages will be or may become apparent to one with skill in the art upon examination of the following drawings and detailed description. It is intended that all such additional systems, methods, features and/or advantages be included within this description and be protected by the accompanying claims.

BRIEF DESCRIPTION OF THE DRAWINGS

The components in the drawings are not necessarily to scale relative to each other. Like reference numerals designate corresponding parts throughout the several views.

FIG. 6A illustrate pre-block conditions (i.e., nerve recordings before application of electrical stimulation for selectively inhibiting neural activity). FIG. 6B illustrate block conditions (i.e., nerve recordings during application of electrical stimulation for selectively inhibiting neural activity). FIG. 6C illustrate post-block conditions (i.e., nerve recordings after application of electrical stimulation for selectively inhibiting neural activity).

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. Ranges may be expressed herein as from "about" one particular value, and/or to "about" another particular value. When such a range is expressed, an aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. While implementations will be described for causing a perturbation of blood glucose level in a subject, it will become evident to those skilled in the art that the implementations are not limited thereto.

Example Device

Figure 1:
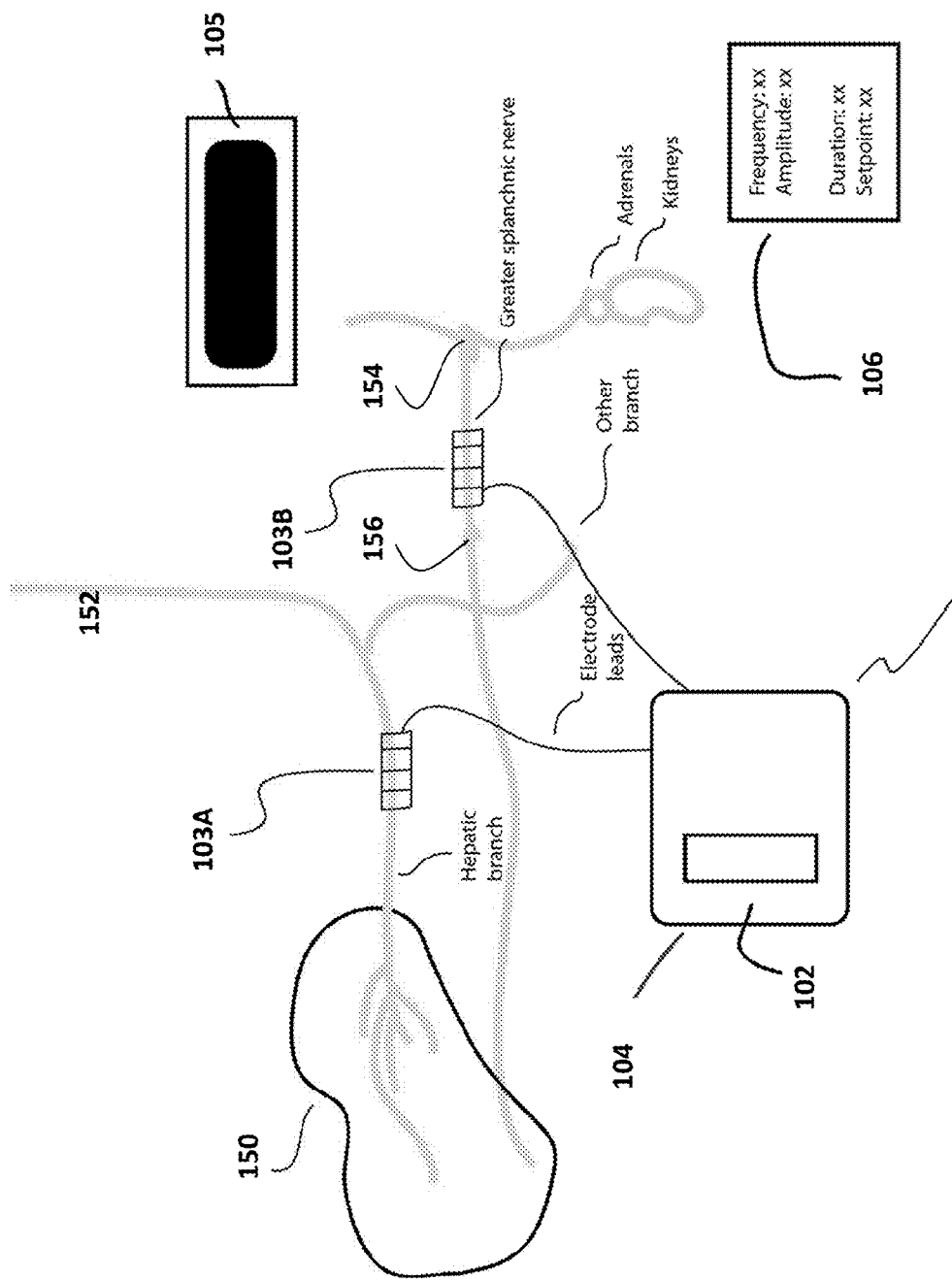
FIG. 1 illustrates an example device for causing a perturbation of blood glucose level in a subject and includes the subject's organs, nerves and example electrode locations.

Referring now to FIG. 1, an example device for causing a perturbation of blood glucose level in a subject is shown. The device 100 can include a first electrode 103A configured to attach to a portion of a hepatic branch of the subject's vagus nerve and a second electrode 103B configured to attach to a portion of the subject's greater splanchnic nerve 103B. The first electrode 103A and the second electrode 103B are referred to collectively herein as electrodes 103. The electrodes 103 can optionally be implanted in the subject's body. Each of the electrodes 103 can be a monopolar, bipolar, or tripolar electrode. For example, the electrodes 103 can be cuff-type electrodes. An example cuff-type electrode is described in U.S. 2016/0001082 to Butera et al., "SELECTIVE BLOCK OF NERVE ACTION POTENTIAL CONDUCTION," filed Jul. 2, 2015. Cuff-type electrodes are known in the art and are therefore not discussed further herein. Alternatively or additionally, the electrodes 103 can be other types of electrodes known in the art including, but not limited to, microneedle-type electrodes, paddle electrodes, or helical cuff electrodes.

The device 100 can also include a stimulus generator 101. The stimulus generator 101 can be battery-powered. The stimulus generator 101 can be operably coupled with the first electrode 103A and the second electrode 103B. This disclosure contemplates that the stimulus generator 101 and the first electrode 103A and the second electrode 103B can be coupled using a wired or wireless (e.g., radiofrequency (RF)) link. The stimulus generator 101 can be configured to provide stimulus signals to at least one of the first electrode 103A and the second electrode 103B. Additionally, the stimulus generator 101 can be a voltage source or a current source. For example, VBLOC MAESTRO System of ENTEROMEDICS, INC. of St. Paul, Minn. includes an implantable stimulus generator that can be used with the implementations described herein. Alternatively or additionally, the stimulus generator 101 can include programmable logic 102, e.g., a processor and memory operably coupled to the processor such as the most basic configuration of example computing device 500 of FIG. 5. The programmable logic 102 can be programmed to control operation of the stimulus generator 101, for example, in the closed-loop configuration described herein. In the closed-loop configuration, the programmable logic 102 is configured to turn on/turn off the stimulus generator 101 when the subject's systemic blood glucose (e.g., as measured by a glucose sensor) decreases below/increases above a set point. Optionally, the stimulus generator 101 can be implanted in the subject's body.

The device 100 can also optionally include a control unit 106. Optionally, the control unit 106 can be implemented as the example computing device 500 of FIG. 5. As shown in FIG. 1, the control unit 106 and the stimulus generator 101 can be separate and distinct units. Optionally, the control unit 106 can be external to the subject' body, i.e., not implanted in the subject's body. The control unit 106 can be operably coupled to the stimulus generator 101 using a communication link. This disclosure contemplates the communication link is any suitable communication link. For example, a communication link can be implemented by any medium that facilitates data exchange between the network elements including, but not limited to, wired, wireless and optical links. Example communication links include, but are not limited to, a LAN, a WAN, a MAN, Ethernet, the Internet, or any other wired or wireless link such as Bluetooth, Wi-Fi, ZigBee, Wi-Max, 3G or 4G. Optionally, the control unit 106 can include a display device (e.g., for displaying the subject's systemic blood glucose) and/or an input device (e.g., a human machine interface for receiving user commands). Optionally, the control unit 106 can include an output device, for example, to provide audible, visible, and/or tactile alarms to the user. The control unit 106 can be configured to control operation of the stimulus generator 101. For example, the control unit 106 can be configured to select or adjust the characteristic of the electrical stimulation (e.g., frequency, current amplitude, timing, etc.). Alternatively or additionally, the control unit 106 can be configured to receive set point(s) from a user. For example, a user (e.g., the subject himself or a third person) can use the control unit 106 to program, set or adjust set points (e.g., systemic blood glucose) at which the stimulus generator turns on/turns off. These operations can occur when the subject's systemic blood glucose (e.g., as measured by a glucose sensor) decreases below/increases above a set point, which is displayed on the display device.

The device 100 can also optionally include a glucose sensor 104. The glucose sensor 104 can be configured for monitoring the subject's blood glucose level. Optionally, the glucose sensor 104 can be implanted in the subject's body. In some implementations, the glucose sensor 104 can be operably coupled to the stimulus generator 101 using a communication link as described herein. Optionally, the glucose sensor 104 can be incorporated into the stimulus generator 101. Optionally, the glucose sensor 104 can be separate and distinct from the stimulus generator 101. Alternatively or additionally, the glucose sensor 104 can be operably coupled to the control unit 106 using a communication link as described herein. The glucose sensor 104 can transmit the subject's blood glucose measurements to the stimulus generator 101, a user input/output device (described below), and/or the control unit 106. As described herein, the subject's measured blood glucose can be used for controlling the device 100 in either closed-loop or open-loop configurations.

The device 100 can also optionally include a user input/output device 105. The user input/output device 105 can be operably coupled to the stimulus generator 101, the glucose sensor 104, and/or the control unit 106 using a communication link as described herein. Optionally, the user input/output device 105 can be external to the subject' body, i.e., not implanted in the subject's body. The user input/output device 105 can include a display device (e.g., for displaying the subject's measured blood glucose) and/or an input device (e.g., a human machine interface for receiving user commands). Optionally, the user input/output device 105 can include an output device, for example, to provide audible, visible, and/or tactile alarms to the user.

Placement of Electrodes

As described above, the first electrode 103A can attach to a portion of a hepatic branch of the subject's vagus nerve. The subject has anterior and posterior hepatic branches of the vagus nerve, and the first electrode 103A can attach to a portion of either the anterior hepatic branch of the vagus nerve or the posterior hepatic branch of the vagus nerve. The second electrode 103B can attach to a portion of the subject's greater splanchnic nerve 103B. The subject has right and left greater splanchnic nerves, and the second electrode 103B can attach to a portion of either the right greater splanchnic nerve or the left greater splanchnic nerve. An example arrangement of the electrodes 103 is shown in FIG. 1. For example, the first electrode 103A can be located between the subject's liver 150 and the subject's anterior and/or posterior vagal trunk 152. Optionally, the first electrode 103A can be located distal to the gastric branches and proximal to the liver 150. Additionally, the second electrode 103B can be located between the subject's suprarenal ganglia 154 and celiac ganglia 156. Optionally, the second electrode 103B can be located on the left and/or right greater splanchnic nerve to minimize effects on other unwanted organs and physiological parameters, such as but not limited to, the adrenals and kidneys. Optionally, the second electrode 103B can be located distal to the celiac ganglia 156 and closer to the liver 150 to optimize stimulation effects. Optionally, the locations of the respective electrodes can be optimized to minimize stimulation and/or block effects on suprarenal ganglia function. It should be understood that the example arrangements described with respect to FIG. 1 are provided only as examples and that other electrode arrangements are possible in accordance with this disclosure.

Stimulus Signals

Figure 2:
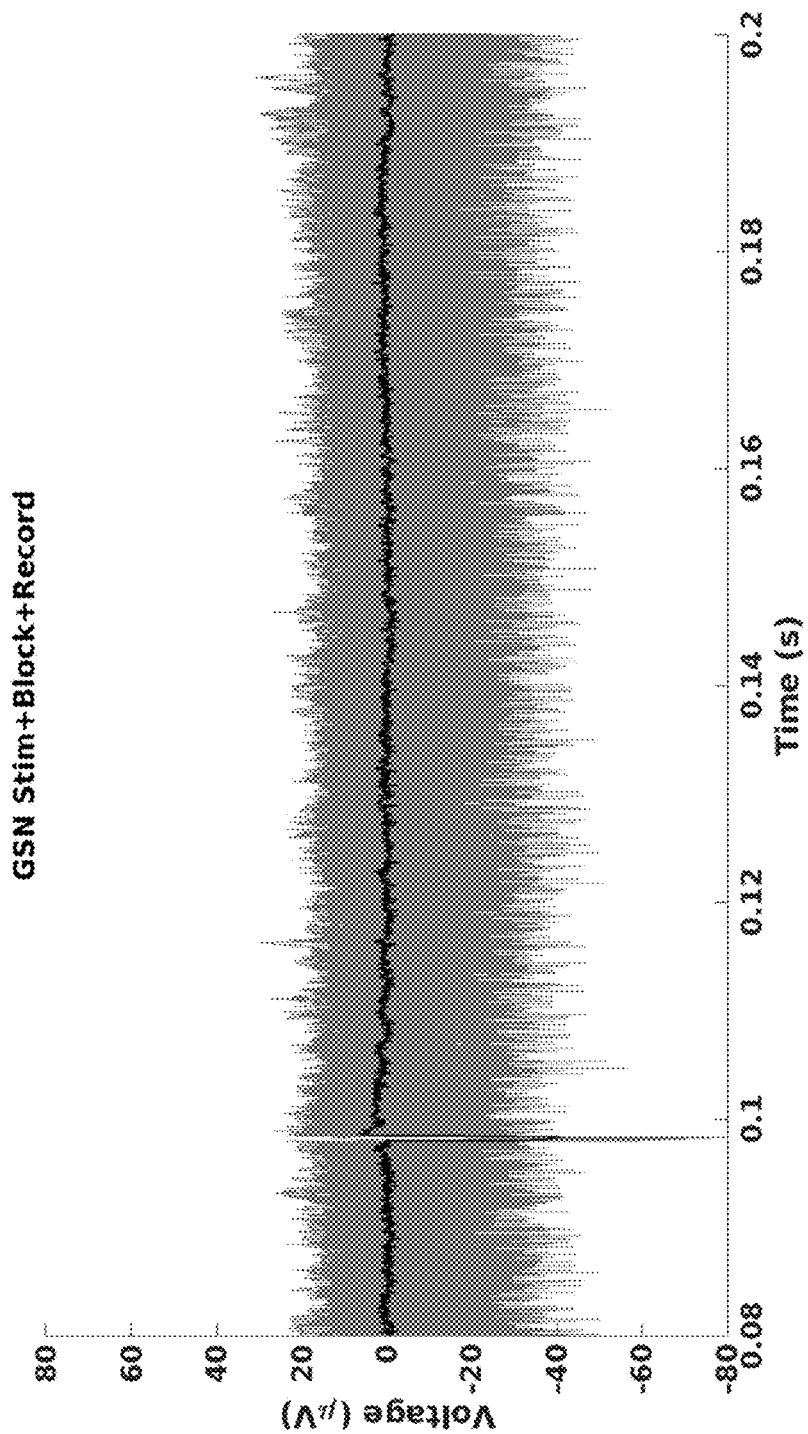
FIG. 2 is a graph illustrating nerve recordings on a nerve where neural activity is selectively inhibited.

Neural activity can be selectively inhibited using electrical stimulation. Neural activity of the hepatic branch of the subject's vagus nerve can be selectively inhibited by applying electrical stimulation via first electrode 103A of FIG. 1. Neural activity of the subject's greater splanchnic nerve can be selectively inhibited by applying electrical stimulation via second electrode 103B of FIG. 1. As used herein, selectively inhibiting neural activity on a nerve means blocking action potential conduction (also referred to herein as "propagating activity") on the nerve. FIG. 2 is a graph that shows nerve recordings on a nerve where neural activity is selectively inhibited using electrical stimulation with kilohertz high frequency alternating current (KHFAC). In some implementations, the application of electrical stimulation results in blocking nearly all propagating activity on a nerve. Alternatively, in some implementations, the application of electrical stimulation results in blocking less than all propagating activity on a nerve (i.e., blocking some propagating activity on a nerve while leaving other propagating activity on the nerve unmolested). Blocking less than all propagating activity on a nerve can reduce unwanted effects of electrical stimulation. The characteristics of the electrical stimulation (e.g., frequency, amplitude, etc.) can be selected to achieve different blocking effects on a nerve.

Figures 6A, 6B, 6C:
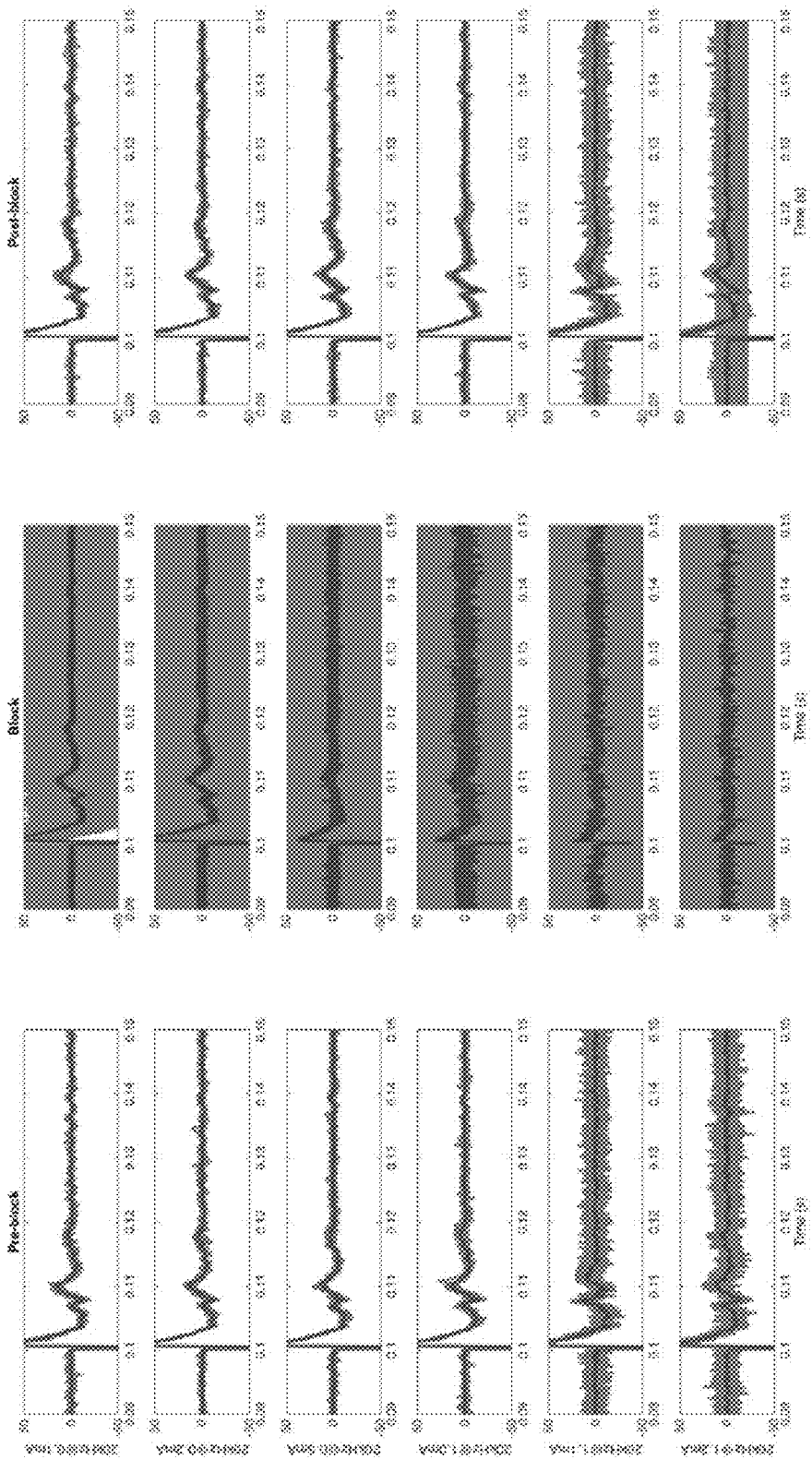
FIGS. 6A-6C are graphs illustrating nerve recordings representing selective levels of blocking neural activity.

FIGS. 6A-6C are graphs illustrating nerve recordings representing selective levels of blocking neural activity. As shown in FIGS. 6A-6C, blocking neural activity by applying electrical stimulation with KHFAC is repeatable and reversible. In other words, the nerve recordings of FIG. 6C return to the pre-block levels of FIG. 6A after application of electrical stimulation, which demonstrates that the electrical stimulation with KHFAC can be turned on/turned off repeatedly without causing damage to the nerve while selectively inhibiting a portion of or all of the nerve activity.

The electrical stimulation for selectively inhibiting neural activity can be electrical stimulation with KHFAC. KHFAC has a frequency greater than or equal to 1 kHz, for example, from about 1 kHz to about 100 kHz. Optionally, KHFAC has a frequency greater than or equal to about 5 kHz, for example, from about 5 kHz to about 100 kHz. Optionally, KHFAC has a frequency from about 5 kHz to about 70 kHz. Optionally, KHFAC has a frequency from about 50 kHz to about 100 kHz. Optionally, KHFAC has a frequency from about 20 kHz to about 70 kHz. In addition, the electrical stimulation for selectively inhibiting neural activity can have various symmetric or asymmetric waveform shapes including, but not limited to, sine waves or square waves. Alternatively or additionally, the electrical stimulation for selectively inhibiting neural activity can deliver a current with an amplitude from about 50 µA to about 50 mA. Optionally, the electrical stimulation for selectively inhibiting neural activity can deliver a current with an amplitude from about 5 mA to about 10 mA.

Figure 3:
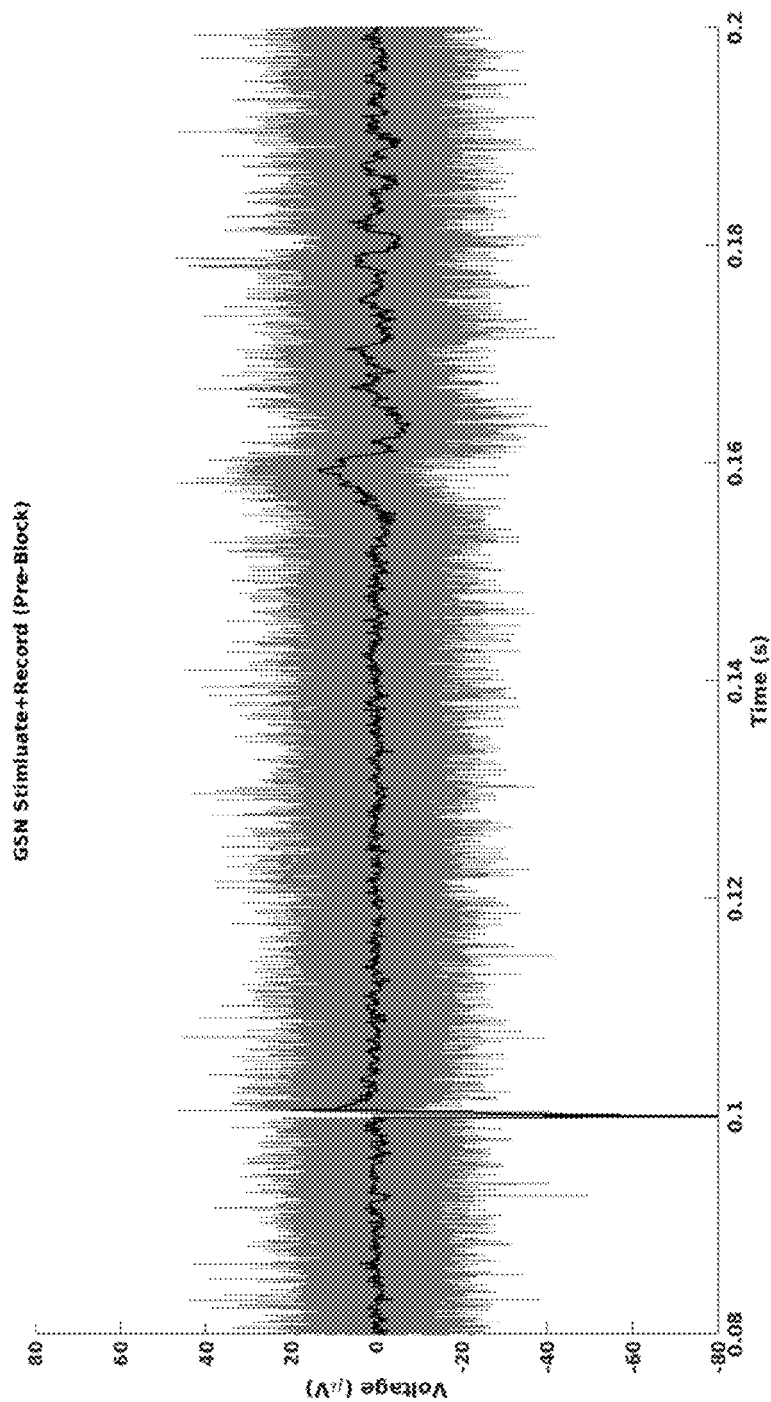
FIG. 3 is a graph illustrating nerve recordings on a nerve where neural activity is selectively excited.

Neural activity can be selectively excited using electrical stimulation. Neural activity of the hepatic branch of the subject's vagus nerve can be selectively excited by applying electrical stimulation via first electrode 103A of FIG. 1. Neural activity of the subject's greater splanchnic nerve can be selectively excited by applying electrical stimulation via second electrode 103B of FIG. 1. As used herein, selectively exciting neural activity on a nerve means increasing propagating activity on a nerve. FIG. 3 is a graph that shows nerve recordings on a nerve where neural activity is selectively excited using electrical stimulation.

The electrical stimulation for selectively exciting neural activity can be electrical stimulation having a frequency from about 1 Hz to about 200 Hz. In addition, the electrical stimulation for selectively exciting neural activity can have various waveform shapes including, but not limited to, monophasic, symmetric biphasic, and asymmetric biphasic. Alternatively or additionally, the duty cycle of the electrical stimulation for selectively exciting neural activity can be modulated from about 10% to about 90%. Alternatively or additionally, the electrical stimulation for selectively exciting neural activity can deliver a current with an amplitude from about 50 µA to about 50 mA. Optionally, the electrical stimulation for selectively exciting neural activity can deliver a current with an amplitude from about 5 mA to about 10 mA.

Figure 4:
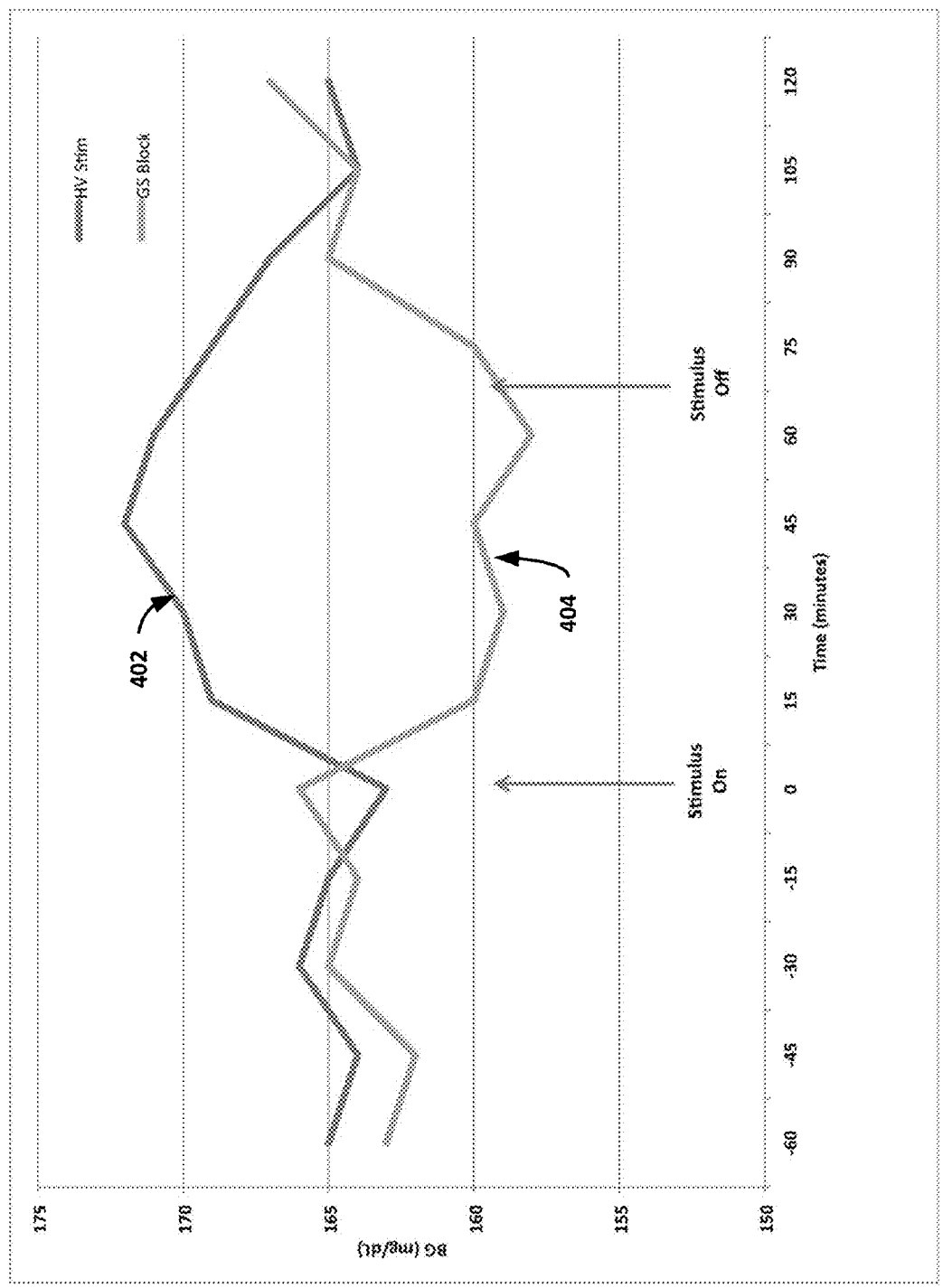
FIG. 4 is a graph that illustrates the results of perturbing blood glucose levels in a subject according to an example described herein.

Referring now to FIG. 4, a graph that illustrates the results of perturbing blood glucose levels in a subject is shown. This example represents one possible combination of electrical stimulation to excite and inhibit neural activity of the vagus nerve and the greater splanchnic nerve, respectively. In particular, the hepatic branch of the vagus nerve was electrically stimulated to excite neural activity. This is represented by line 402 of FIG. 4, where blood glucose level begins to increase at about time 0 when electrical stimulation is applied. Additionally, the greater splanchnic was electrically stimulated to inhibit neural activity. This is represented by line 404 of FIG. 4, where blood glucose level begins to decrease at about time 0 when electrical stimulation with KHFAC stimulation is applied. Average blood glucose levels before, during, and after electrical stimulation to excite the hepatic branch of the vagus nerve and to inhibit the greater splanchnic nerve are shown. Blood glucose measurements were made every 15 minutes using over the counter blood glucose strips. Three measurements were made at every time point, and the average values are plotted in FIG. 4.

Electrical stimulation was achieved using a respective tripolar cuff electrode attached to a portion of the hepatic branch of the vagus nerve and a portion of the greater splanchnic nerve. The hepatic branch of the vagus nerve was stimulated with cathode first, biphasic stimulation pulses in voltage mode of 5 V at 10 Hz, 50% duty cycle. The greater splanchnic nerve was electrically stimulated with KHFAC stimulation to inhibit nerve activity using a charge-balanced periodic waveform in current mode of 1 mA at 50 kHz.

Example Methods

Electrical stimulation of the hepatic vagus nerve and/or the greater splanchnic nerve allows for drug-free modulation of systemic blood glucose levels. It should be understood that the implementations described below are provided only as examples and that other device configurations and/or methods can be used in accordance with this disclosure. For example, it is possible for the device described herein to be used in conjunction with existing therapies to reduce the load on a subject with diminished pancreatic function. For example, it could enhance the efficacy of oral therapies used for subjects with type II diabetes.

An example method for causing a perturbation of blood glucose level in a subject is described below. It should be understood that the device 100 of FIG. 1 can optionally be used to cause the perturbation of blood glucose level in the subject. According to this example method, neural activity of at least one of a hepatic branch of the subject's vagus nerve or the subject's greater splanchnic nerve can be selectively inhibited using electrical stimulation with KHFAC as described herein. The characteristics of the electrical stimulation for inhibiting neural activity are described above. The electrical stimulation for inhibiting neural activity can be applied to the hepatic branch of the subject's vagus nerve and the subject's greater splanchnic nerve via the first and second electrodes 103A and 103B, respectively, of FIG. 1. The placement of the electrodes for providing electrical stimulation to the vagus nerve and the splanchnic nerve are described above. The selective inhibition of neural activity causes the subject's blood glucose level to increase or decrease as compared to a baseline level. The selective inhibition of neural activity can also cause a change in level of a metabolite or enzyme (i.e., other than blood glucose) as compared to a baseline level. Example metabolites include, but are not limited to, Glucose-1-phosphate, Glucose-6-phosphate, or Glycogenin. Example enzymes include, but are not limited to, Glucose 6-phosphatase, Glucokinase, Hexokinase, or Glycogen branching enzyme.

Optionally, this example method can further include selectively exciting neural activity of at least one of the hepatic branch of the subject's vagus nerve or the subject's greater splanchnic nerve using electrical stimulation. The characteristics of the electrical stimulation for exciting neural activity are described above. The electrical stimulation for exciting neural activity can be applied to the hepatic branch of the subject's vagus nerve and the subject's greater splanchnic nerve via the first and second electrodes 103A and 103B, respectively, of FIG. 1. The placement of the electrodes for providing electrical stimulation to the vagus nerve and the splanchnic nerve are described above. The selective excitation and inhibition of neural activity causes the subject's blood glucose level to increase or decrease as compared to a baseline level. The selective excitation and inhibition of neural activity can also cause a change in level of a metabolite or enzyme (i.e., other than blood glucose) as compared to a baseline level. Example metabolites include, but are not limited to, Glucose-1-phosphate, Glucose-6-phosphate, or Glycogenin. Example enzymes include, but are not limited to, Glucose 6-phosphatase, Glucokinase, Hexokinase, or Glycogen branching enzyme.

In one example implementation, neural activity of the hepatic branch of the subject's vagus nerve can be selectively excited. For example, an electrode (e.g., the first electrode 103A of FIG. 1) can be attached to a portion for the hepatic branch of the subject's vagus nerve as described above, and electrical stimulation having a frequency from about 1 Hz to about 200 Hz and current with an amplitude 50 µA-50 mA can be applied via this electrode. Additionally, neural activity of the subject's splanchnic nerve can be selectively inhibited. For example, an electrode (e.g., second electrode 103B of FIG. 1) can be attached to a portion for the subject's splanchnic nerve as described above, and electrical stimulation with KHFAC (e.g., having a frequency from about 5 kHz to about 100 kHz) and current with an amplitude 100 µA-100 mA can be applied via this electrode. It should be understood that exciting the hepatic branch of the subject's vagus nerve and inhibiting the subject's splanchnic nerve is provided only as an example.

Optionally, in some implementations, the method can further include monitoring the subject's blood glucose level. For example, the subject's blood glucose level can be monitored using a glucose sensor (e.g., glucose sensor 104 of FIG. 1) as described herein. The method can further include controlling the selective excitation or inhibition of neural activity based on the subject's blood glucose level.

Another example method for causing a perturbation of blood glucose level in a subject is described herein. It should be understood that the device 100 of FIG. 1 can optionally be used to cause the perturbation of blood glucose level in the subject. According to this example method, a first electrode (e.g., first electrode 103A of FIG. 1) can be provided at a portion of a hepatic branch of the subject's vagus nerve, and a second electrode (e.g., first electrode 103B of FIG. 1) can be provided at a portion of the subject's greater splanchnic nerve. Additionally, a stimulus generator (e.g., stimulus generator 101 of FIG. 1) can be provided. The stimulus generator can be operably coupled with the first electrode and the second electrode as described herein.

Then, using the stimulus generator, a first stimulus signal can be provided to the first electrode. The first stimulus signal can be configured to energize the first electrode and excite neural activity of the hepatic branch of the subject's vagus nerve. The characteristics of electrical stimulation for exciting neural activity are described above (e.g., frequency 1 Hz-200 Hz, current with an amplitude 50 μA-50 mA). Additionally, using the stimulus generator, a second stimulus signal can be provided to the second electrode. The second stimulus signal can be configured to energize the second electrode and inhibit neural activity of the subject's greater splanchnic nerve. The characteristics of electrical stimulation for inhibiting neural activity are described above (e.g., frequency 1 kHz-100 kHz, current with an amplitude 100 μA-110 mA). As described herein, the subject's blood glucose level increases and/or decreases as compared to a baseline level in response to providing the first stimulus or providing the second stimulus signal.

Open Loop Device Control

It should be understood that the device 100 of FIG. 1 can optionally be used to cause the perturbation of blood glucose level in the subject. The device can be controlled in an open loop mode with user control. For example, the device can include a stimulation unit (e.g., stimulus generator 101), first and second electrodes (e.g., first and second electrodes 103A and 103B of FIG. 1), a glucose sensor (e.g., glucose sensor 104 of FIG. 1), and an input/output device (e.g., user input/output device 105 of FIG. 5). In an open loop mode, the device can be turned on/turned off by a user (e.g., manually) using the input/output device. The input/output device provides the user with measurement information (e.g., systemic blood glucose levels) along with controls and the option to turn the electrical stimulation on/off to excite or inhibit neural activity in either or both nerves, and thus increase or decrease systemic blood glucose. The user can be the subject whose blood glucose levels are being perturbed or a third party (e.g., a medical professional or clinician). For example, the user can turn on the device 30 minutes before a meal and then turn off the device 2 hours after the meal. It should be understood that these times for turning on/turning off the device are provided only as examples.

Closed Loop Device Control

It should be understood that the device 100 of FIG. 1 can optionally be used to cause the perturbation of blood glucose level in the subject. The device can be controlled in a closed loop mode with a programmable interface for user control. For example, the device can include a stimulation unit (e.g., stimulus generator 101) with programmable logic (e.g., programmable logic 102 of FIG. 1), first and second electrodes (e.g., first and second electrodes 103A and 103B of FIG. 1), a glucose sensor (e.g., glucose sensor 104 of FIG. 1), an input/output device (e.g., user input/output device 105 of FIG. 1), and a control unit (e.g., control unit 106 of FIG. 1). The device provides a programmable interface for the user to set or adjust a blood glucose level set point(s). The stimulation unit therefore has a logic controller that can be configured to turn on/off when the systemic blood glucose level falls below or rises above a programmed set point(s). The stimulation unit can be configured to turn on/turn off automatically in response to the subject's blood glucose level, which can be monitored by the glucose sensor. In other words, the device can be configured to electrically stimulate the hepatic vagus and/or the greater splanchnic nerve to increase or decrease neural activity, which can increase or decrease systemic blood glucose levels of the subject. Optionally, systemic blood glucose levels can also be provided to the user via the input/output device.

Alternatively, the device can be controlled in a closed loop mode with autonomous control for setting systemic blood glucose levels. For example, the device can include a stimulation unit (e.g., stimulus generator 101), first and second electrodes (e.g., first and second electrodes 103A and 103B of FIG. 1), and a glucose sensor (e.g., glucose sensor 104 of FIG. 1). The device can be pre-configured with a blood glucose level set point(s). For example, the stimulation unit can be configured to an initial set point(s) based on blood glucose levels measured prior to implantation of the electrodes/stimulation unit. The device can measure systemic blood glucose levels using the glucose sensor, and automatically adjust the electrical stimulation to either increase and/or decrease neural activity in the hepatic vagus nerve and/or the greater splanchnic nerve to maintain the set point(s). The device can automatically adjust the set point for desired systemic blood glucose and automatically adjust the stimulation to increase and/or decrease nerve activity in either nerve. In other words, the device can be programed to use the initial set point(s) as a starting point and then calibrate the set point(s) over time based upon the user's metabolic changes.

Glucose Loading

The device 100 of FIG. 1 can optionally be used for modulating the amount of glucose loaded before, during, and after a bolus. For example, a substance (e.g., a bolus of glucose, a meal, food, etc.) can be administered to the subject. The substance can be administered to the subject orally or through injection. The subject's blood glucose level can then be measured (e.g., using glucose sensor 104 of FIG. 1), for example at each of a plurality of time intervals, to obtain information about how the subject's body clears glucose. Additionally, one or more characteristics of electrical stimulation (e.g., stimulation parameters) can be adjusted based on the subject's measured blood glucose level to optimize effects of stimulation, and a glucose load associated with the substance can be altered through the selective excitation or inhibition of neural activity.

Example Computing Device

It should be appreciated that the logical operations described herein with respect to the various figures may be implemented (1) as a sequence of computer implemented acts or program modules (i.e., software) running on a computing device (e.g., the computing device described in FIG. 5), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 5:
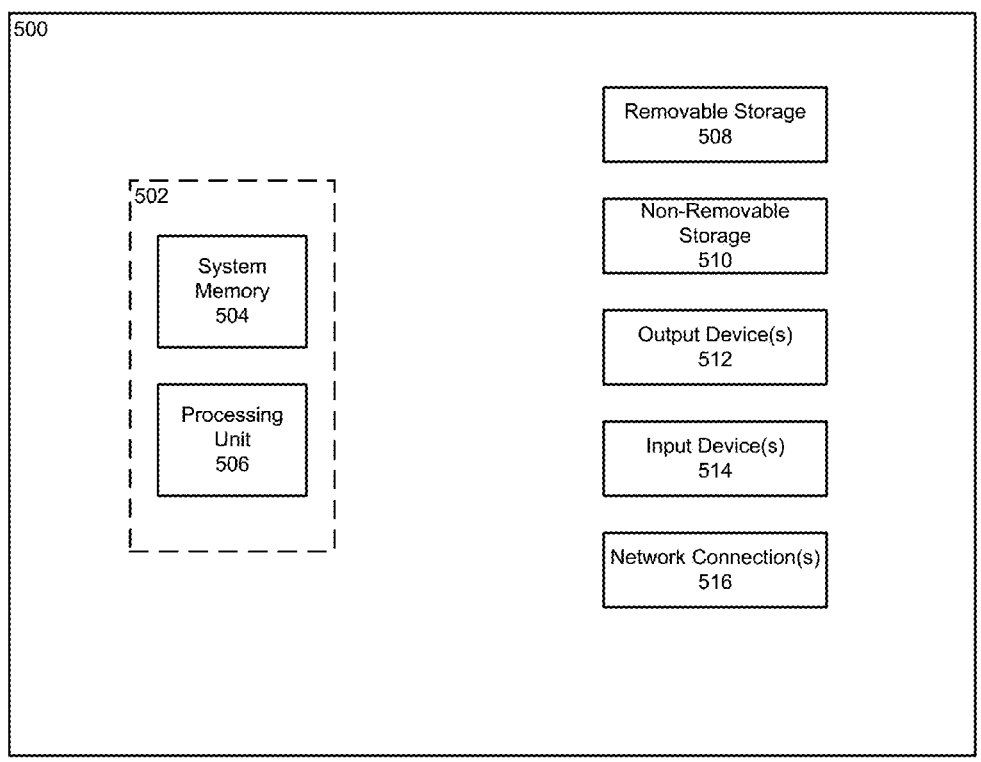
FIG. 5 is an example computing device.

Referring to FIG. 5, an example computing device 500 upon which embodiments of the invention may be implemented is illustrated. It should be understood that the example computing device 500 is only one example of a suitable computing environment upon which embodiments of the invention may be implemented. Optionally, the computing device 500 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 500 typically includes at least one processing unit 506 and system memory 504. Depending on the exact configuration and type of computing device, system memory 504 may be volatile (such as random access memory (RAM)), non-volatile (such as read-only memory (ROM), flash memory, etc.), or some combination of the two. This most basic configuration is illustrated in FIG. 5 by dashed line 502. The processing unit 506 may be a standard programmable processor that performs arithmetic and logic operations necessary for operation of the computing device 500. The computing device 500 may also include a bus or other communication mechanism for communicating information among various components of the computing device 500.

Computing device 500 may have additional features/functionality. For example, computing device 500 may include additional storage such as removable storage 508 and non-removable storage 510 including, but not limited to, magnetic or optical disks or tapes. Computing device 500 may also contain network connection(s) 516 that allow the device to communicate with other devices. Computing device 500 may also have input device(s) 514 such as a keyboard, mouse, touch screen, etc. Output device(s) 512 such as a display, speakers, printer, etc. may also be included. The additional devices may be connected to the bus in order to facilitate communication of data among the components of the computing device 500. All these devices are well known in the art and need not be discussed at length here.

The processing unit 506 may be configured to execute program code encoded in tangible, computer-readable media. Tangible, computer-readable media refers to any media that is capable of providing data that causes the computing device 500 (i.e., a machine) to operate in a particular fashion. Various computer-readable media may be utilized to provide instructions to the processing unit 506 for execution. Example tangible, computer-readable media may include, but is not limited to, volatile media, non-volatile media, removable media and non-removable media implemented in any method or technology for storage of information such as computer readable instructions, data structures, program modules or other data. System memory 504, removable storage 508, and non-removable storage 510 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 506 may execute program code stored in the system memory 504. For example, the bus may carry data to the system memory 504, from which the processing unit 506 receives and executes instructions. The data received by the system memory 504 may optionally be stored on the removable storage 508 or the non-removable storage 510 before or after execution by the processing unit 506.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Abbreviations
BG: blood glucose
mA: milliamps
Hz: hertz
kHz: kilohertz
mg/dl: milligrams per decaliter
V: volts Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed:

1. A method for causing a perturbation of blood glucose level in a subject, comprising:
selectively inhibiting neural activity of at least one of a hepatic branch of the subject's vagus nerve or the subject's greater splanchnic nerve using electrical stimulation having a frequency about 50 kHz or greater, wherein the selective inhibition of neural activity causes the subject's blood glucose level to increase or decrease as compared to a baseline level.

2. The method of claim 1, further comprising selectively exciting neural activity of at least one of the hepatic branch of the subject's vagus nerve or the subject's greater splanchnic nerve using electrical stimulation, wherein the selective excitation and inhibition of neural activity causes the subject's blood glucose level to increase or decrease as compared to the baseline level.

3. The method of claim 2, wherein neural activity of the hepatic branch of the subject's vagus nerve is selectively excited using electrical stimulation.

4. The method of claim 1, wherein neural activity of the subject's greater splanchnic nerve is selectively inhibited using electrical stimulation having a frequency about 50 kHz or greater.

5. The method of claim 1, wherein the electrical stimulation delivers a current with an amplitude from about 100 μA to about 10 mA.

6. The method of claim 2, wherein neural activity of at least one of the hepatic branch of the subject's vagus nerve or the subject's greater splanchnic nerve is selectively excited using electrical stimulation having a frequency from about 1 Hz to about 200 Hz.

7. The method of claim 6, wherein the electrical stimulation delivers a current with an amplitude from about 50 μA to about 50 mA.

8. The method of claim 1, further comprising:
administering a substance to the subject;
measuring the subject's blood glucose level at each of a plurality of time intervals;
adjusting one or more stimulation parameters based on the subject's measured blood glucose level; and
altering a glucose load associated with the substance through the selective excitation or inhibition of neural activity.

9. The method of claim 8, wherein the substance is administered to the subject orally or through injection.

10. The method of claim 1, wherein the selective excitation or inhibition of neural activity further causes a change in level of a metabolite.

11. The method of claim 1, further comprising providing a first electrode at a portion of the hepatic branch of the subject's vagus nerve and a second electrode at a portion of the subject's greater splanchnic nerve.

12. The method of claim 11, wherein the first electrode is provided between the subject's liver and the subject's vagal trunk.

13. The method of claim 11, wherein the second electrode is provided between the subject's suprarenal ganglia and celiac ganglia.

14. The method of claim 11, wherein at least one of the first electrode or the second electrode is a monopolar, bipolar, or tripolar electrode.

15. The method of claim 1, further comprising monitoring the subject's blood glucose level.

16. The method of claim 15, further comprising controlling the selective excitation or inhibition of neural activity based on the subject's blood glucose level.

17. The method of claim 1, further comprising controlling the selective excitation or inhibition of neural activity based on user input.

18. The method of claim 1, further comprising controlling the selective excitation or inhibition of neural activity based on a predetermined time schedule.

19. The method of claim 1, wherein neural activity of at least one of the hepatic branch of the subject's vagus nerve or the subject's greater splanchnic nerve is selectively inhibited using electrical stimulation having a frequency from 50 kHz to 100 kHz.

20. A device for causing a perturbation of blood glucose level in a subject, comprising:
a first electrode configured to attach to a portion of a hepatic branch of the subject's vagus nerve;
a second electrode configured to attach to a portion of the subject's greater splanchnic nerve;
a stimulus generator operably coupled with the first electrode and the second electrode, the stimulus generator being configured to provide stimulus signals to at least one of the first electrode and the second electrode; and
a control unit operably coupled with the stimulus generator, the control unit comprising a processor and memory operably coupled to the processor, wherein the control unit is configured to control the stimulus generator to:
provide a first stimulus signal configured to selectively excite neural activity of at least one of the hepatic branch of the subject's vagus nerve or the subject's greater splanchnic nerve; and
provide a second stimulus signal having a frequency about 50 kHz or greater and configured to selectively inhibit neural activity of at least one of the hepatic branch of the subject's vagus nerve or the subject's greater splanchnic nerve, wherein the selective excitation and inhibition of neural activity causes the subject's blood glucose level to increase or decrease as compared to a baseline level.

* * * * *